United States Patent [19]

Cheng

[11] 4,097,262
[45] Jun. 27, 1978

[54] HERBICIDAL ACETAMIDES

[75] Inventor: Jiin-Duey Cheng, Wilmington, Del.

[73] Assignee: E. I. Du Pont de Nemours and Company, Wilmington, Del.

[21] Appl. No.: 789,961

[22] Filed: Apr. 22, 1977

[51] Int. Cl.² .................................... A01W 9/12; A01W 9/22; C07D 236/04; C07D 277/04
[52] U.S. Cl. ............................. 71/90; 71/88; 260/306.7 R; 260/307C
[58] Field of Search ............ 71/88, 90; 260/306.7 R, 260/307 C

[56] References Cited

U.S. PATENT DOCUMENTS 4,055,410  10/1977  Cheng ..................... 260/306.7 R

*Primary Examiner*—Donald G. Daus
*Assistant Examiner*—D. B. Springer

[57] ABSTRACT

Herbicidal bromo- or chloroacetamides of the formula:

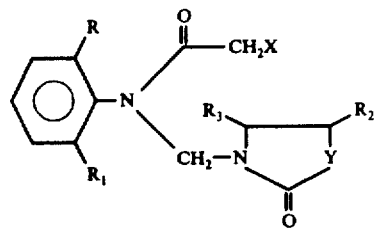

where
  R is alkyl or alkoxy of 1 to 4 carbon atoms;
  $R_1$ is hydrogen or alkyl of 1 to 3 carbon atoms;
  $R_2$ is hydrogen or methyl;
  $R_3$ is hydrogen or methyl;
  X is chlorine or bromine; and
  Y is oxygen or sulfur.

40 Claims, No Drawings

HERBICIDAL ACETAMIDES

BACKGROUND OF THE INVENTION

Recently in U.S. Pat. Nos. 3,769,301 and 3,907,544 herbicidal compounds of the general formula:

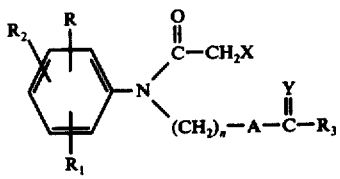

where
X is halogen;
n is 1 or 2;
A is, among others, $-N-(CO)_m-R_4$; where
   m is 0, 1, or 2; and
   $R_3$ and $R_4$ together can form an alkylene bridge or 2-5 carbons; and
Y is oxygen or sulfur,
were disclosed.

The compounds taught within these patents are active herbicides; the need still exists, however, for herbicides which are more active. The presence of undesired vegetation is very damaging to useful crops such as rice. In the current world situation, wherein food shortages are acute, it is most important to maximize the yields of valuable crops, such as rice. The presence of weeds results in the loss of a significant portion of such crop. Thus, a need exists for a herbicide which will effectively control weeds without causing significant damage to the crop, e.g. rice.

According to the instant invention, herbicidal compounds have been discovered which are highly active herbicides and yet cause minimal damage to certain desired crops, e.g. rice.

DESCRIPTION OF THE INVENTION

This invention relates to novel compounds of Formula I to agricultural compositions containing them and to the method of use of these compounds as selective herbicides for the pre-emergence control of grasses, particularly barnyardgrass in rice.

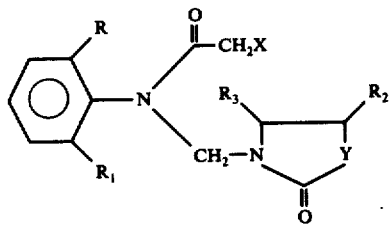

where
R is alkyl or alkoxy of 1 to 4 carbon atoms;
$R_1$ is hydrogen or alkyl of 1 to 3 carbon atoms;
$R_2$ is hydrogen or methyl;
$R_3$ is hydrogen or methyl;
X is chlorine or bromine; and
Y is oxygen or sulfur.

Preferred for their high herbicidal activity, favorable cost or both are those compounds where, independently, (1) R is alkyl or alkoxy of 1 to 2 carbon atoms; or
(2) $R_1$ is hydrogen, methyl or ethyl; or
(3) $R_2$ is hydrogen; or
(4) $R_3$ is hydrogen.

More preferred for their higher herbicidal activity, more favorable cost or both are those compounds where R and $R_1$ are methyl or ethyl.

Most preferred for their excellent herbicidal activity, highly favorable cost or both are those compounds of Formula I where both R and $R_1$ are methyl or ethyl and $R_2$ and $R_3$ are both hydrogen.

Specifically preferred for their outstanding herbicidal activity, highly favorable cost or both are:

(1) 2-Chloro-N-(2-ethyl-6-methylphenyl)-N-[(2-oxooxazolidin-3-yl)methyl]acetamide, m.p. 101°-102.5° C.
(2) 2-Chloro-N-(2,6-diethylphenyl)-N-[(2-oxooxazolidin-3-yl)methyl]acetamide, m.p. 125°-127° C.
(3) 2-Chloro-N-(2-ethyl-6-methylphenyl)-N-[(2-oxothiazolidin-3-yl)methyl]acetamide, m.p. 89°-91° C.

DETAILED DESCRIPTION OF THE INVENTION

The novel compounds of this invention are prepared by haloacetylation of the corresponding anilines of Formula II in an aprotic solvent such as toluene, chloroform or benzene in the presence of an acid acceptor as shown by Equation A.

The reaction takes place at a temperature of about −30° to 80° C, preferably −10° to 5° C over a period of about 30 minutes to 5 hrs, preferably about 1 to 3 hrs.

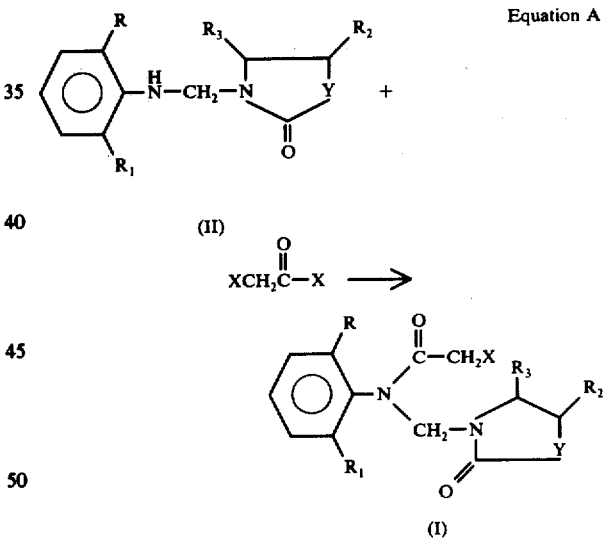

Equation A

Intermediate anilines of Formula II can be prepared by condensation of a primary aniline of Formula III, formaldehyde, and a 2-oxazolidone or 2-thiazolidone of Formula IV in a protic or aprotic solvent at 10° to 150° C under atmospheric pressure, as shown by Equation B. The reaction is base catalyzed. It is preferred to run the reaction in either ethanol or N,N-dimethylformamide (DMF) at 25° to 90° C by using metal alkoxide or metal hydroxide as the base catalyst. For convenience, compounds of Formula II with only one substituent on the benzene ring are prepared by reaction of a substituted aniline of Formula III, formaldehyde, and a compound of Formula IV with a catalytic amount of sodium methoxide in ethanol either at ambient temperature or under reflux for 2 to 20 hrs. Compounds of Formula II having substituents in both the 2 and 6 position of the benzene ring are prepared by reaction of an N-methylene aniline of formula (V) with a compound of formula IV in the presence of sodium methoxide in DMF at 20° to 80° C for 2 to 20 hrs. N-Methylene anilines of formula V can be prepared according to the procedure of J. Org. Chem. 34, 1192 (1969) which is herein incorporated by reference.

Equation B

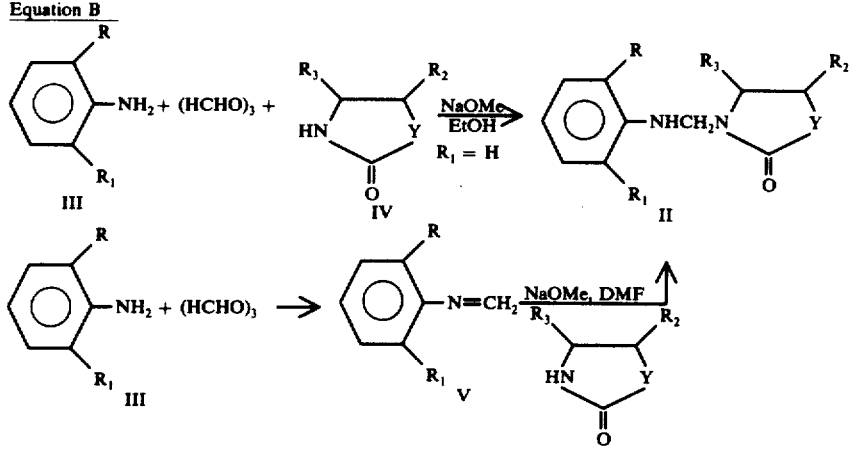

The following examples are offered to illustrate the processes described above.

EXAMPLE 1

3-(2-Methoxyphenylaminomethyl)-2-oxazolidone

A mixture of 12.3 g of o-anisidine, 8.7 g of 2-oxazolidone and 3.3 g of paraformaldehyde in 80 ml of absolute ethanol was heated to reflux under a nitrogen atmosphere. After 30 min, 1 g of sodium methoxide was added to the solution and reflux was continued for 4 hrs. At the end of this time solvent was removed by means of a rotary evaporator and the residue was dissolved in chloroform. The chloroform solution was washed twice with two 50 ml portions of water, dried over anhydrous magnesium sulfate, filtered and the filtrate concentrated in vacuo. The residual oil was crystallized from a mixture of ether and n-hexane to give 8 g of 3-(2-methoxyphenylaminomethyl)-2-oxazolidone, mp 95.5° – 98° C.

EXAMPLE 2

N-(2-Methoxyphenyl)-N-[(2-oxooxazolidin-3-yl)methyl]-2-chloroacetamide

A solution of 4.5 g of chloroacetyl chloride in 20 ml of toluene was added dropwise to a suspension of 6.7 g of 3-(2-methoxyphenylaminomethyl)-2-oxazolidone and 3 g of pyridine in 40 ml of toluene. The temperature was not permitted to exceed −10° C during the addition. After the addition, the mixture was stirred on an ice bath for 3 hrs. The precipitate was collected by filtration, washed thoroughly with water and ether, and air-dried to give 7.2 g of N-(2-methoxyphenyl)-N-[(2-oxooxazolidin-3-yl)methyl]-2-chloroacetamide, mp 109°–110° C. Recrystallization from a mixture of methylene chloride and ether gave a solid with a mp of 110°–110.5° C.

EXAMPLE 3

3-(2-Ethyl-6-methylphenylaminomethyl)-2-oxazolidone

A mixture of 14.7 g of N-methylene-2-methyl-6-ethylaniline, 8.8 g of 2-oxazolidone, and 0.5 g of sodium methoxide in 20 ml of dry N,N-dimethylformamide was heated at 60° C for 13 hrs under a nitrogen atmosphere. On cooling, 100 ml of ether was added and the solution was washed with four portions each of 50 ml of water. The ether layer was dried over anhydrous magnesium sulfate, filtered and the filtrate was concentrated to give an oil. The oil was triturated with cold n-hexane containing a small amount of ether to give 8.5 g of 3-(2-ethyl-6-methylphenylaminomethyl)-2-oxazolidone, mp 56°–57.5° C.

EXAMPLE 4

N-(2-Ethyl-6-methylphenyl)-N-[(2-oxooxazolidin-3-yl)methyl]-2-chloroacetamide

A solution of 2.8 g of chloroacetyl chloride in 10 ml of toluene was added dropwise to a solution of 4.2 g of 3-(2-ethyl-6-methylphenylaminomethyl)-2-oxazolidone and 1.8 g of pyridine in 40 ml of toluene at temperature below −10° C. The suspension was stirred on an ice bath for 2 hrs. The precipitate was collected by filtration, washed thoroughly with water and air-dried to give 4.6 g of N-(2-ethyl-6-methylphenyl)-N-[(2-oxooxazolidin-3-yl)methyl]-2-chloroacetamide, mp 101°–102.5° C.

The following compounds of formula I can be prepared by the procedures described in examples 1–4.

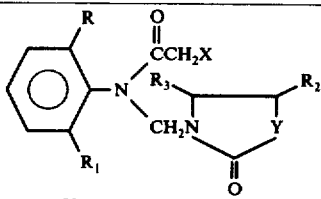

| R | $R_1$ | X | Y | $R_2$ | $R_3$ | Melting Point° C |
|---|---|---|---|---|---|---|
| $CH_3$ | H | Cl | O | H | H | 105–106° |
| $CH_3$ | $C_2H_5$ | Cl | O | $CH_3$ | H | 94–98° |
| $C_2H_5$ | $C_2H_5$ | Cl | O | H | H | 125–127° |
| i-$C_3H_7$ | H | Cl | O | H | H | oil |
| $C_2H_5$ | $C_2H_5$ | Cl | O | $CH_3$ | H | 98–100° |
| $C_2H_5O$ | H | Cl | O | H | H | 141.5–142.5° |
| $C_2H_5$ | H | Cl | O | H | H | 77.5–80° |
| sec-$C_4H_9$ | H | Cl | O | H | H | |
| $CH_3$ | $C_2H_5$ | Cl | O | H | $CH_3$ | 106–129° |
| $C_2H_5$ | $C_2H_5$ | Cl | O | H | $CH_3$ | 103–104.5° |
| $CH_3$ | i-$C_3H_7$ | Cl | O | H | H | |
| $CH_3$ | $CH_3$ | Cl | O | H | H | 120–121.5° |
| $CH_3$ | $C_2H_5$ | Br | O | H | H | |
| $C_2H_5$ | $C_2H_5$ | Br | O | H | H | |
| $CH_3$ | $C_2H_5$ | Cl | O | $CH_3$ | $CH_3$ | 124.5–127° |

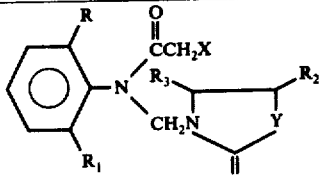

| R | R₁ | X | Y | R₂ | R₃ | Melting Point° C |
|---|---|---|---|---|---|---|
| $C_2H_5$ | $C_2H_5$ | Cl | O | $CH_3$ | $CH_3$ |  |
| $CH_3$ | $CH_3$ | Cl | S | H | H | 132–133.5° |
| $CH_3$ | $C_2H_5$ | Cl | S | H | H | 89–91° |
| $C_2H_5$ | $C_2H_5$ | Cl | S | H | H | 87–89° |
| $CH_3$ | H | Cl | S | H | H | 107–112° |
| $CH_3$ | $C_2H_5$ | Cl | S | $CH_3$ | H |  |
| $CH_3O$ | H | Cl | S | H | H | 103–104° |
| sec-$C_4H_9$ | $CH_3$ | Cl | S | H | H |  |
| n-$C_4H_9O$ | H | Cl | S | H | H |  |
| $CH_3$ | $C_2H_5$ | Br | S | H | H |  |
| $CH_3$ | $C_2H_5$ | Br | S | $CH_3$ | $CH_3$ |  |
| $C_2H_5$ | $C_2H_5$ | Br | S | $CH_3$ | $CH_3$ |  |
| $C_2H_5$ | $C_2H_5$ | Br | S | H | H |  |
| $CH_3$ | i-$C_3H_7$ | Cl | S | H | H |  |
| i-$C_3H_7$ | i-$C_3H_7$ | Cl | S | H | H |  |
| i-$C_3H_7$ | i-$C_3H_7$ | Cl | O | H | H |  |

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1 to 99% by weight of active ingredient(s) and at least one of a) about 0.1 to 20% surfactant(s) and b) about 1 to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publ. Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The method of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4the Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

In the following Examples all parts are by weight and all temperatures in ° C unless otherwise indicated.

EXAMPLE 5

| Granule | |
|---|---|
| 2-chloro-N-(2-ethyl-6-methylphenyl)-N-[(2-oxothiazolidin-3-yl)methyl]-acetamide | 10% |
| attapulgite granules (low volatile Matter, 0.71/0.30 mm; U.S.S. # 25–50 sieves) | 90% |

The active ingredient is warmed to approximately 100° C and sprayed upon dedusted and pre-warmed attapulgite granules in a double cone blender. The granules are then allowed to cool and are packaged.

EXAMPLE 6

| Extruded Pellet | |
|---|---|
| 2-chloro-N-(2-ethyl-6-methylphenyl)-N-[(2-oxooxazolidin-3-ylmethyl]-acetamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

| Aqueous Suspension | |
|---|---|
| 2-chloro-N-(2,6-diethylphenyl)-N-[(2-oxooxazolidin-3-yl)methyl]-acetamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns. The materials are then strained through a U.S.S. No. 50 sieve and packaged.

EXAMPLE 8

| Solution | |
|---|---|
| 2-chloro-N-(2-ethyl-6-methylphenyl)-N-[(2-oxothiazolidin-3-yl)methyl]-acetamide | 30% |
| dimethylformamide | 70% |

The ingredients are combined and stirred to produce a solution, which can be used for low volume applications.

EXAMPLE 9

| Wettable Powder | |
|---|---|
| 2-chloro-N-(2-ethyl-6-methylphenyl)-N-[(2-oxooxazolidin-3-yl)methyl]-acetamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

EXAMPLE 10

| Wettable Powder | |
|---|---|
| 2-chloro-N-(2-ethyl-6-methylphenyl)-N-[(2-oxothiazolidin-3-yl)methyl]acetamide | 80% |
| sodium alkylnaphthalenesulfonate | 2% |
| sodium ligninsulfonate | 2% |
| synthetic amorphous silica | 3% |
| kaolinite | 13% |

The ingredients are blended, coarsely hammer-milled and then air-milled to produce particles essentially all below 10 microns on size. The material is reblended and packaged.

EXAMPLE 11

| High Strength Concentrate | |
|---|---|
| 2-chloro-N-(2-ethyl-6-methylphenyl)-N-[(2-oxooxazolidin-3-yl)methyl]-acetamide | 99% |

| -continued | |
|---|---|
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

All compounds of the invention may be formulated in the same manner.

Utility

The compounds of Formula I are useful for the control of undesired vegetation in crops. More particularly, the compounds of the present invention control barnyard-grass (*Echinochloa spp.*) and other undesired vegetation in rice, corn, soybean, and other crop cultures.

The compounds of the present invention are most effective against barnyardgrass and other weeds when applied prior to emergence of the weeds from the soil. They may be applied in upland (dry) cultures or in paddy (flooded) cultures.

The precise amount of the compounds of the present invention to be used will vary according to the cultural method employed, the soil type, weather, etc. However, broadly speaking, they are used at rates of about 0.05 kg to about 10 kg, preferably 0.25 to 4 kg per hectare. The lower rates in this range will generally be selected on sandy soils low in organic matter content or in situations where maximum persistence is not necessary.

The compounds of the present invention may be applied singly or in admixture with other herbicides, including but not restricted to: 2,4-dichlorophenyl-4'-nitrophenylether; 2-methylthio-4,6-bis(ethylamino)-s-triazine; ethyl hexahydrothiol-1-azepinecarboxylate, 2,4-dichlorophenoxyacetic acid and salts thereof; 4-amino-6-tert-butyl-3-(methylthio)-1,2,4-triazin-5(4H)-one; and 3-(3,4-dichlorophenyl)-1-methoxy-1-methylurea.

The herbicial activity of the compounds of the present invention was discovered in a number of greenhouse tests. The following tables illustrate the activity of compounds of the present invention.

Procedure, Test 1

Seeds of crabgrass(*Digitaria sp.*), barnyardgrass (*Echinochloa crusgalli*), wild oats (*Avena fatua*), Cassia *tora*, morningglory (*Ipomoea spp.*), cocklebur (*Xanthium sp.*), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the second trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to controls and visually rated for response to treatment.

Ratings for compounds tested by this procedure are recorded in Table 1.

The plant response ratings shown are composed of a number and a letter. The number describes the extent of the response and ranges from 0 to 10 with 0 representing no response, and 10 representing 100% response. The letter describes the type of the response, with "B" representing burn, "C" representing chlorosis-necrosis, "D" representing defoliation, "E" representing emergence inhibition, "G" growth retardation, "H" formative effect (malformation or hormone type), "I" increased chlorophyll, and "P" terminal bud injury.

TABLE 1

POST EMERGENCE

| COMPOUND | Kg per Hectare | BUSH BEAN | COT-TON | MORN-ING GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| [structure: ethyl/chloroacetyl oxazolidinone on 2,6-disubstituted phenyl] | 2 | 4D | 0 | 2H | 0 | 0 | 5G | 8G | 9H | 8H | 1C 7G | 5G | 1H | 8G | 5G |
| [structure: methyl/chloroacetyl oxazolidinone] | 2 | 1B 3G | 1B 3G | 1B 3H | 0 | 3G | 7G | 9G | 9H | 8H 5I | 8G 5I | 7H | 2H | 8G 5I | 9H 5I |
| [structure: methyl/chloroacetyl thiazolidinone] | 2 | 1H | 0 | 0 | 0 | 0 | — | 8G | 9H | 8G | 2G | 2H 6G | 0 | 10P 9G | 2G |

PRE-EMERGENCE

| COMPOUND | Kg per Hectare | MORN-ING GLORY | COCKLE-BUR | CAS-STA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|

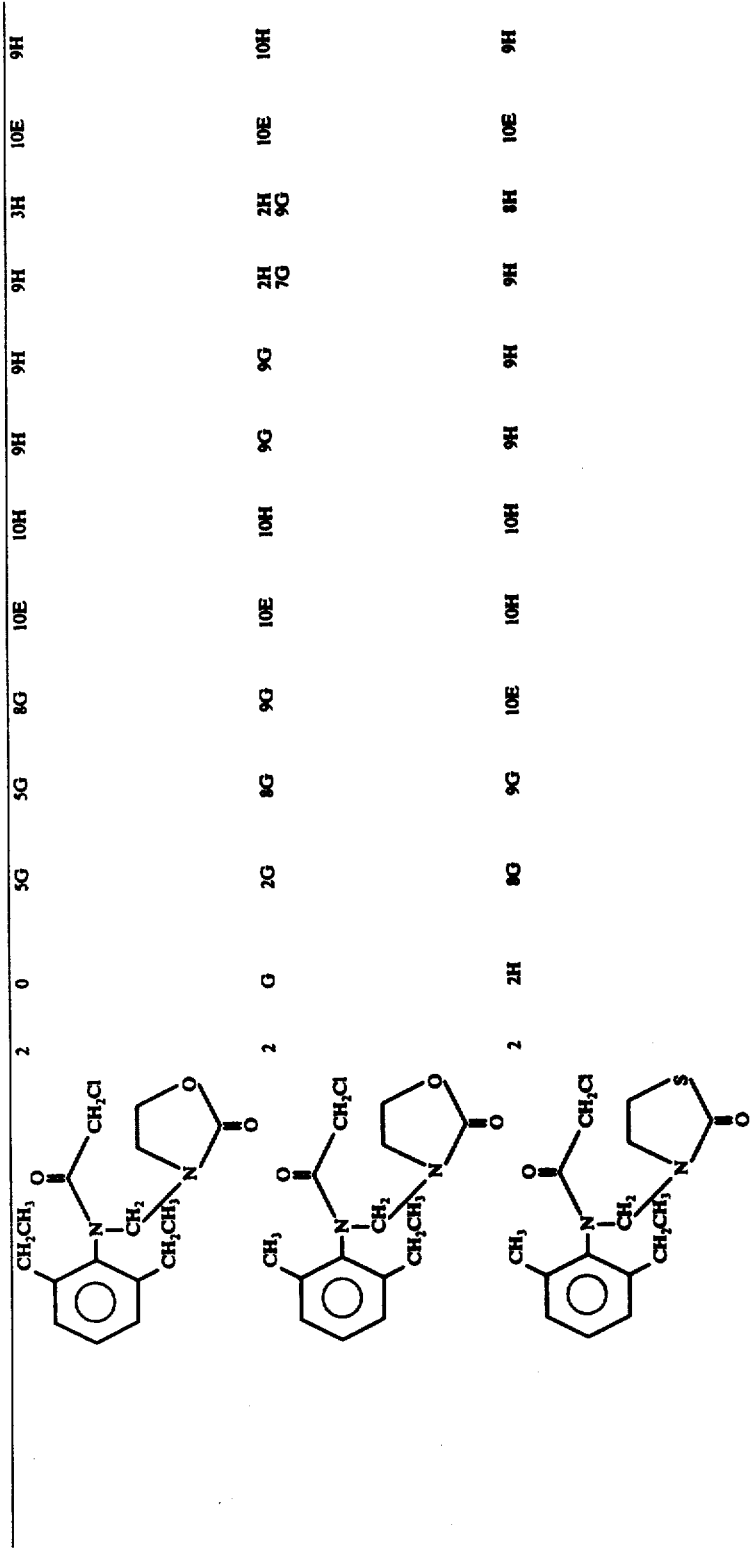

Procedure, Test 2

A medium-textured soil, fairly low in organic matter content, was planted with seeds of the species listed in the following table. Planting depth was about 0.5 cm except for corn and soybeans which were planted at a depth of 2.5 cm. The test compounds were dissolved/suspended in a nonphytotoxic solvent. Within a few hours of planting, the test solutions were applied to the soil surface. The rates of application for the test compounds are shown in the table. Immediately after treatment the soil surfaces were exposed to simulated rainfall at the rate of approximately 5 mm of water over a period of 180 minutes. From this point the plantings were maintained in the greenhouse and watered on a demand basis. Plant response ratings made around 4 weeks after planting and treatment, are recorded in Table 2.

The same rating procedure and symbols as mentioned in Test 1 apply for Test 2.

TABLE 2

| COMPOUND | Rate Kg/ha | Crab-grass | Barn-yard grass | Sor-ghum | Wild Oats | John-son grass | Dal-las-grass | Gi-ant Fox-tail | Ky. Blue-grass | Cheat-grass | Corn | Mus-tard | Cock-le-but | Pig-weed | Nut-sedge | In-di-go | Morn-ing-glory | Cas-sia | Tea-weed | Vet-vet-leaf | Jim-son-weed | Soy-bean | Rice | Wheat | Sug-ar-beets |
|---|---|---|---|---|---|---|---|---|---|---|---|---|---|---|---|---|---|---|---|---|---|---|---|---|---|
| 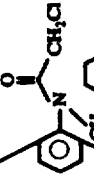 | 4 1 | 9H 10E | 8H 10H | 0 7H | 6H 8H | 5H 8H | — — | 6H 9H | 9H 10H | 5H 9H | 0 0 | 0 0 | 0 0 | 0 9H | 0 6G | — — | 0 0 | 0 8H | 0 0 | 0 0 | 0 0 | 0 5G | 6H 10H | 3H 6H | 0 0 |
| 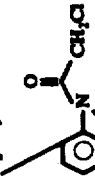 | 4 1 | 10H 10H | 10H 10H | 4H 9H | 2H 8H | 3H 10H | — — | 9H 10H | 7H 10H | 6H 10H | 0 0 | 0 0 | 0 0 | 0 10E | 4H 7H | 10H 10E | 0 0 | 0 0 | 0 0 | — — | 0 0 | 3G — | 3H 9H | 4G 6H | 0 0 |
| 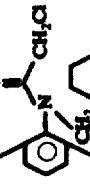 | 4 1 | 10H 10H | 10H 10H | 4H 10H | 2H 7H | 3H 10H | 8H 10H | 6H 10H | 8H 10H | 0 7H | 0 5H | 0 2G | — 0 | 10C 10C | — — | — — | — 3G | — — | — — | — — | 0 2C | 0 0 | 2H 10H | 0 6H | 0 4C |

Procedure, Test 3

Table 3 is presented to further illustrate the biological activity of the compounds of this invention.

The test compounds were applied in a non-phytotoxic solvent to pots containing soil and seeds of an intermediate hybrid rice, japonica rice, barnyardgrass (*Echinochloa crusgalli*), morning glory (*Ipomoea sp.*), wheat, wild oats (*Avena fatua*), downy brome (*Bromus tectorum*), and cheat (*Bromus secalinus*). The plants were maintained in a greenhouse and visual plant response ratings (as described in Table 1) were taken three weeks after application.

TABLE 4

| COMPOUND | RATE kg ai/ha | Japonica Rice | Barnyard-grass |
|---|---|---|---|
| (structure with CH₂CH₃, CH₂Cl, CH₃) | 1 | 0 | 10C |

TABLE 3

PRE-EMERGENCE

| COMPOUND | RATE kg ai/ha | Intermediate Rice | Japonica rice | Barn-yard-grass | Morning-glory | Wheat | Wild Oats | *Bromus tectorum* | *Bromus secatinus* |
|---|---|---|---|---|---|---|---|---|---|
| (structure 1: CH₂CH₃, CH₂Cl, CH₂CH₃) | 1/8 | 0 | 0 | 9G | 0 | — | — | — | — |
|  | 1/4 | 10E | 5G | 5H | 0 | — | — | — | — |
|  | 1/2 | 6G | 5G | 10C | 0 | — | — | — | — |
|  | 1 | 9C | 8G | 10C 10C | 1G | — | — | — | — |
| (structure 2: CH₂CH₃, CH₂Cl, CH₃) | 1/16 | 0 | 0 | 7H | 0 | — | — | — | — |
|  | 1/8 | 0 | 0 | 9H | 0 | — | — | — | — |
|  | 1/4 | 0 | 4G | 10C | 0 | — | — | — | — |
|  | 1/2 | 6G | 6G | 10C | — | — | — | — | — |

|  |  | PRE-EMERGENCE |  |  |  |  |  |  |  | POST EMERGENCE |  |  |  |  |  |
|---|---|---|---|---|---|---|---|---|---|---|---|---|---|---|---|
| COMPOUND | Rate kg ai/ha | Nato Int. Rice | cs-m3 Jpn Rice | Barn-yard-grass | Morn-ing-glory | Wheat | Wild Oats | Bromus tec-torum | Bromus se-cal-inus | Nato Int. Rice | cs-m3 Jpn Rice | Barn-yard-grass | Morn-ing-glory | Wheat | Wild Oats |
| (structure: CH₂CH₃, CH₂Cl, CH₃, S) | ½ | — | 1G | 9C | — | 1G | 7E | 0 | 7G | | | | | | |
|  | 1 | 10E | 4G | 10C | 0 | 3G | 10C | 7E | 10E | | | | | | |

Procedure, Test 4

Table 4 is presented to additionally illustrate the biological activity of the compounds of the present invention. The data illustrate the herbicidal efficacy of the compounds with selectivity for rice in paddy culture.

A rice paddy was constructed using a tub containing soil and barnyardgrass (*Echinochloa crusgalli*) seeds, and japonica rice plants which were transplanted into the paddy soil when in the three to four leaf stage. The water level was maintained a few centimeters above the soil surface. The test sample was applied directly into the paddy water, and plant response ratings were taken three weeks later.

What is claimed is:

1. A compound of the formula

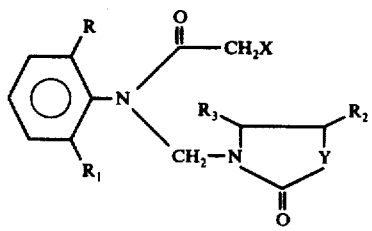

where
R is alkyl or alkoxy of 1 to 4 carbon atoms;
R₁ is hydrogen or alkyl of 1 to 3 carbon atoms:
R₂ is hydrogen or methyl;

$R_1$ is hydrogen or methyl;

X is chlorine or bromine; and

Y is oxygen or sulfur.

2. A compound of claim 1 wherein R is alkyl or alkoxy of 1 to 2 carbon atoms.

3. A compound of claim 1 wherein $R_1$ is hydrogen, methyl or ethyl.

4. A compound of claim 1 wherein $R_2$ is hydrogen.

5. A compound of claim 1 wherein $R_3$ is hydrogen.

6. A compound of claim 1 wherein R and $R_1$ are methyl or ethyl.

7. A compound of claim 1 wherein R and $R_1$ are methyl or ethyl and $R_2$ and $R_3$ are both hydrogen.

8. The compound of claim 1, 2-chloro-N-(2-ethyl-6-methylphenyl)-N-[(2-oxooxazolidin-3-yl)methyl]acetamide.

9. The compound of claim 1, 2-chloro-N-(2,6-diethylphenyl)-N-[(2-oxooxazolidin-3-yl)methyl]acetamide.

10. The compound of claim 1, 2-chloro-N-(2-ethyl-6-methylphenyl)-N-[(2-oxothiazolidin-3-yl)methyl]acetamide.

11. A composition for the control of undesirable vegetation consisting essentially of a herbicidally effective amount of a compound of claim 1 and at least one of (a) a surface-active agent and (b) a solid or liquid diluent.

12. A composition for the control of undesirable vegetation consisting essentially of a herbicidally effective amount of a compound of claim 2 and at least one of (a) a surface-active agent and (b) a solid or liquid diluent.

13. A composition for the control of undesirable vegetation consisting essentially of a herbicidally effective amount of a compound of claim 3 and at least one of (a) a surface-active agent and (b) a solid or liquid diluent.

14. A composition for the control of undesirable vegetation consisting essentially of a herbicidally effective amount of a compound of claim 4 and at least one of (a) a surface-active agent and (b) a solid or liquid diluent.

15. A composition for the control of undesirable vegetation consisting essentially of a herbicidally effective amount of a compound of claim 5 and at least one of (a) a surface-active agent and (b) a solid or liquid diluent.

16. A composition for the control of undesirable vegetation consisting essentially of a herbicidally effective amount of a compound of claim 6 and at least one of (a) a surface-active agent and (b) a solid or liquid diluent.

17. A composition for the control of undesirable vegetation consisting essentially of a herbicidally effective amount of a compound of claim 7 and at least one of (a) a surface-active agent and (b) a solid or liquid diluent.

18. A composition for the control of undesirable vegetation consisting essentially of a herbicidally effective amount of the compound of claim 8 and at least one of (a) a surface-active agent and (b) a solid or liquid diluent.

19. A composition for the control of undesirable vegetation consisting essentially of a herbicidally effective amount of the compound of claim 9 and at least one of (a) a surface-active agent and (b) a solid or liquid diluent.

20. A composition for the control of undesirable vegetation consisting essentially of a herbicidally effective amount of the compound of claim 10 and at least one of (a) a surface-active agent and (b) a solid or liquid diluent.

21. A method for the control of undesirable vegetation comprising applying to the locus of such undesirable vegetation a herbicidally effective amount of a compound of claim 1.

22. A method for the control of undesirable vegetation comprising applying to the locus of such undesirable vegetation a herbicidally effective amount of a compound of claim 2.

23. A method for the control of undesirable vegetation comprising applying to the locus of such undesirable vegetation a herbicidally effective amount of a compound of claim 3.

24. A method for the control of undesirable vegetation comprising applying to the locus of such undesirable vegetation a herbicidally effective amount of a compound of claim 4.

25. A method for the control of undesirable vegetation comprising applying to the locus of such undesirable vegetation a herbicidally effective amount of a compound of claim 5.

26. A method for the control of undesirable vegetation comprising applying to the locus of such undesirable vegetation a herbicidally effective amount of a compound of claim 6.

27. A method for the control of undesirable vegetation comprising applying to the locus of such undesirable vegetation a hebicidally effective amount of a compound of claim 7.

28. A method for the control of undesirable vegetation comprising applying to the locus of such undesirable vegetation a herbicidally effective amount of the compound of claim 8.

29. A method for the control of undesirable vegetation comprising applying to the locus of such undesirable vegetation a herbicidally effective amount of the compound of claim 9.

30. A method for the control of undesirable vegetation comprising applying to the locus of such undesirable vegetation a herbicidally effective amount of the compound of claim 10.

31. A method for the control of barnyardgrass in rice comprising applying to the locus of such barnyardgrass a herbicidally effective amount of a compound of claim 1.

32. A method for the control of barnyardgrass in rice comprising applying to the locus of such barnyardgrass a herbicidally effective amount of a compound of claim 2.

33. A method for the control of barnyardgrass in rice comprising applying to the locus of such barnyardgrass a herbicidally effective amount of a compound of claim 3.

34. A method for the control of barnyardgrass in rice comprising applying to the locus of such barnyardgrass a herbicidally effective amount of a compound of claim 4.

35. A method for the control of barnyardgrass in rice comprising applying to the locus of such barnyardgrass a herbicidally effective amount of a compound of claim 5.

36. A method for the control of barnyardgrass in rice comprising applying to the locus of such barnyardgrass a herbicidally effective amount of a compound of claim 6.

37. A method for the control of barnyardgrass in rice comprising applying to the locus of such barnyardgrass a herbicidally effective amount of a compound of claim 7.

38. A method for the control of barnyardgrass in rice comprising applying to the locus of such barnyardgrass a herbicidally effective amount of the compound of claim 8.

39. A method for the control of barnyardgrass in rice comprising applying to the locus of such barnyardgrass a herbicidally effective amount of the compound of claim 9.

40. A method for the control of barnyardgrass in rice comprising applying to the locus of such barnyardgrass a herbicidally effective amount of the compound of claim 10.

* * * * *